United States Patent [19]

Anderson et al.

[11] Patent Number: 4,818,531

[45] Date of Patent: Apr. 4, 1989

[54] GROWTH HORMONE AND THYROID HORMONE

[75] Inventors: David B. Anderson; Jack F. Wagner, both of Greenfield, Ind.

[73] Assignee: Eli Lilly and Company, Indianapolis, Ind.

[21] Appl. No.: 698,669

[22] Filed: Feb. 6, 1985

[51] Int. Cl.$^4$ .............................................. A61K 37/02
[52] U.S. Cl. ....................................... 424/111; 514/12
[58] Field of Search ........................... 424/111; 514/12

[56] References Cited

U.S. PATENT DOCUMENTS

| | | | |
|---|---|---|---|
| 2,591,107 | 4/1952 | Turner et al. | 99/2 |
| 2,902,406 | 9/1959 | Eibert | 424/111 |
| 4,493,828 | 1/1985 | Leung et al. | 424/177 |

FOREIGN PATENT DOCUMENTS

| | | | |
|---|---|---|---|
| 80854 | 6/1983 | European Pat. Off. | 1/165 |
| 85036 | 8/1983 | European Pat. Off. | 37/36 |
| 104933 | 4/1984 | European Pat. Off. | 37/36 |
| 1130849 | 10/1968 | United Kingdom . | |

OTHER PUBLICATIONS

Davis et al., *J. Anim. Sci.* 42 1244 (1976), Influence of Chronic Thyrotropin-Releasing Hormone Injections on Secretion of Prolactin, Thyrotropin & Growth Hormone & on Growth Rate in Wether Lambs.
Davis et al., *Prostaglandins*, 13 1209 (1977) Influence of Prostaglandins & Thyrotropin Releasing Hormone (TRH) on Hormone Secretion & Growth in Wether Lambs.
Davis et al., *Endocrinology*, 100 1394 (1977) Growth Rate & Secretion of Pituitary Hormones in Relation to Age & Chronic Treatment with Thyrotropin-Releasing Hormone in Prepubertal Dairy Heifers.
McGuffy et al., *J. Anim. Sci.*, 44 422 (1977). Growth, Serum Growth Hormone, Thyroxine, Prolactin & Insulin in Calves After Thyrotropin Releasing Hormone or 3-Methyl-Thyrotropin Releasing Hormone.
Peel et al., *J. Dairy Sci.*, 66 776–782 (1983), Effect of Exogenous Growth Hormone in Early & Late Lactation on Lactational Performance of Dairy Cows.
Bowen et al., *Proc. South. Poul. Sci. Soc.*, Jan. 17–18, 1984, Influence of Chicken Growth Hormone & Tri-iodothyronine on Growth in Normal, Sex-Linked Dwarf & Autosomal Dwarf White Leghorn Chickens.
Harvey et al., *Horm. Metabol. Res.*, 17 113–114 (1985), Interaction Between Human Pancreatic Growth Hormone Releasing Factor (hpGRF) & Thyrotropin Releasing Hormone (TRH) on Growth Hormone Secretion in Domestic Fowl.
Hodate et al., *Endoclinol. Japon.*, 32 375–383 (1985) Growth Hormone, Thyrotropin & Prolactin Responses to Simultaneous Administration of Human Growth Hormone-Releasing Factor & Thyrotropin Releasing Hormone in the Bovine.
Leung et al., *Domestic Animal Endocrinology*, 2 183–190 (1985) Potent Interaction Between Thyrotropin Releasing Hormone (TRH) & Human Pancreatic Growth Hormone Releasing Factor (hpGRF) in Stimulating Chicken Growth Hormone (cGH) in vivo: Hypothalamic Noradrenergic Mediation in TRH Stimulation of cGH Release.
Zanoboni et al., *Neuroendocrinol. Lett.*, 7 289–295 (1985), TRH Does Not Interfere with Growth Hormone Release Induced by GH-RH in Normal Man.
Sorkin et al., *Fed. Proc.*, 45 1614 (1986) Effects of Growth (G) and Thyroid ($T_3$) Hormones on the Rates of Calcium Uptake in Liver Mitochondria (M) of Hypophysectomized Rats.
Rapuano et al., *Fed. Proc.*, 45 2678 (1986) Effects of Growth (GH) & Thyroid ($T_3$) Hormones on t-Butyl-Hydroperoxide (t-B)-Induced Calcium Release in Liver Mitochondria (M) of Hypophysectomized Rats (H).
Hart et al., *J. Endocrinol.*, 108:5 312 (1986) Effects of Thyrotropin-Releasing Hormone on Growth Hormone Secretion in the Presence of Growth Hormone-Releasing Hormone: Differences between the Responses of Ovine & Bovine Anterior Pituitary Cells.
Looij et al., *Clinical Endocrinology*, 24 149–156 (1986) the Interaction of Growth Hormone Releasing Hormone with Other Hypothalamic Hormones on the Release of Anterior Pituitary Hormones.
Szabo *Am. J. Physiol.*, 250 E512–E517 (1986) TRH & GRF Stimulate Release of Growth Hormone through Different Mechanisms.
Wagner, J., et al., *J. Anim. Sci.*, 47, (Suppl. 1), 397 (1978).
Machlin L., et al., *J. Anim. Sci.*, 35 (4), 794–800 (1972).
Machlin, L., *Environmental Quality & Safety*, vol. 5 (Supplement) 43–53 (1976).
Baile, C., et al., *Growth*, 47, 225–236 (1983).
Spence, C., et al., *J. Anim. Sci.*, 59, (Suppl. 1), 246 (1984).
Turman, E., et al., *J. Anim. Sci.*, 14(1), 7–18 (1955).
Frohman, L., et al., *Science*, 162, 580–582 (1968).
Anderson, L., et al., *J. Endocr.*, 68, 345–346 (1976).
Chung, C., et al., *J. Anim. Sci.*, 57, (Suppl. 1), 190 (1983).
Symchowicz, S., et al., *J. Endocr.*, 35, 379–383 (1966).
Vale, W., et al., *Endocrinology*, 112(4), 1553–1555 (1984).
Borges, J., et al., *Endocrinology*, 113(4), 1519–1521 (1983).
Leung, F., et al., *Endocrinology*, 112(5), 1913–1915 (1983).
Oslage, H., et al., *Energy Metabolism*, 297–306 (K. L. Blaxter ed., Academic Press, N.Y., 1965).
Lind, K., et al., *J. Anim. Sci.*, 29, 125 (1969).
Leung et al., *Endocrinology*, 115 (No. 2), 736–740 (1984).

Primary Examiner—Ronald W. Griffin
Assistant Examiner—F. T. Moezie
Attorney, Agent, or Firm—Kathryn R. S. Page; Leroy Whitaker

[57] ABSTRACT

This invention describes a method of increasing the feed intake of pigs, chickens, or dairy cattle, which have elevated levels of growth hormone, by administering a thyroid-active substance.

11 Claims, No Drawings

GROWTH HORMONE AND THYROID HORMONE

BACKGROUND OF THE INVENTION

It is well known that increasing the feed consumption or intake of an animal will increase the weight, or in the case of dairy cow or lactating cow, the milk production of the animal. For example, increasing the growth and weight of the animal brings it to market weight in a shorter period of time, resulting in a substantial savings to the grower.

Although animals always have certain blood levels of growth hormone or related substances, when the growth hormone level is increased above normal, the feed intake or consumption of certain animals decreases. Therefore, it is important to increase the feed intake of these animals, such as pigs and chickens, since they suffer from a feed intake depression. We have discovered that the administration of thyroid-active substances (also including thyrotropic principles) increase the feed intake of those animals, which have above-normal or elevated blood levels of growth hormone.

When dairy cattle have above-normal blood levels of growth hormone, their milk production increases, but their feed intake does not increase nor decrease. This means that the dairy cow is producing more milk without additional feed. It is advantageous to increase the cow's feed intake and, thereby, further increase the quality and quantity of milk production. Therefore, the administration to thyroid-active substances to dairy cattle to increase feed intake is also a part of this invention.

SUMMARY OF THE INVENTION

This invention concerns a method of increasing the feed intake of pigs, chickens, or dairy cattle, who have been treated with a growth hormone related substance, resulting in elevated blood levels of growth hormone or factor, which comprises administering an effective amount of a thyroid-active substance to the pigs, chickens, or dairy cattle.

DETAILED DESCRIPTION OF THE INVENTION

It has now been discovered that pigs (including lactating sows), chickens and dairy cattle, which have elevated levels of growth hormone, resulting in a feed-intake depression for pigs and chickens, or the lack of an increase in feed intake for cattle, can have their feed intake increased by the administration of thyroid-active substances.

The type of thyroid-active substance administered to the pigs, chickens, and dairy cattle includes iodinated casein, thyroprotein, thyroid hormone, thyroid (thyroglobulin, thyroidine, or proloid), $T_4$ (tetraiodothyronine, L-thyroxine, or levothyroxine), or $T_3$ (triiodothyronine, liothyronine, tertroxin, or cytomel). In addition, substances that stimulate the thyroid to produce $T_4$ or $T_3$ can also be administered and include: TSH (thyroid-stimulating hormone, thyrothropin, thyrotropic hormone, thytropar, ambinon, or DERMATHYCIN TM), TRH (thyrotropin-releasing hormone), and the like. The administration of iodinated casein is preferred.

The method of this invention is preferably practiced by orally administering an effective amount of the thyroid-active substance to the animal. However, other routes of administration can be employed, for instance by implant or by intramuscular or intravenous injection. For oral administration, the thyroid-active substance is preferably admixed with suitable carriers or diluents commonly employed in animal husbandry, such as animal feedstuffs. Typical carriers and diluents commonly employed in feedstuffs include corn meal, soybean meal, alfalfa meal, rice hulls, soybean mill run, cottonseed oil meal, bone meal, ground corn, corncob meal, sodium chloride, urea, cane molasses, and the like. These carriers promote a uniform distribution of the thyroid-active substance in the finished feed ration, thereby, ensuring proper distribution of the thyroid-active substance throughout the feed.

While the preferred method for orally administering the thyroid-active substance is through the daily feed rations, it can be incorporated into salt blocks and mineral licks, as well as being added directly to drinking water for convenient oral consumption. Additionally, it can be formulated with polymorphous materials, waxes, and the like, for long-term controlled release, and administered to an animal as a bolus or only as needed to maintain the desired daily payout of the thyroid-active substance.

For parenteral administration, the thyroid-active substance can be mixed with conventional carriers, such as corn oil, sesame oil, carbowax, calcium stearate, and the like. These formulations can be administered as an injection or as a slow-release subcutaneous implant. Other types of implants can also be used to administer the thyroid-active substances and can be located subcutaneously. These implants include silastic implants; polymeric implants, such as polyurethanes, hydrogels, and the like; microcapsules; microspheres; liposomes; and the like. The implant can be removed at the end of the desired administration period. In addition, the thyroid-active substance can be administered by mechanical pumping devices, osmotic, and chemical pumps, and the like.

The amount of thyroid-active substance to be administered to an animal is an amount that is effective in causing an increase in the feed consumption or intake. The effective amount to be administered will vary somewhat depending upon the particular animal species being treated and the form of the thyroprotein administered. For example, the amount of iodinated casein that can be used is from about 50 to about 1000 mg/day (milligrams per day) and the length of time for administration is about 1–5 months for pigs (the length of the finishing period) or about 6–9 months for dairy cattle (the length of the lactation period).

Iodinated casein also can be administered from about 1 to 1000 ppm (parts per million) of the total daily feed intake. This amount will provide a dosage of about 0.05 to about 50 mg/kg/day (milligrams per kilogram per day). A preferred embodiment employs about 1 to about 500 ppm, and more preferably from about 5 to 250 ppm. A typical amount of active ingredient to be administered to pigs will be from about 25 to about 150 ppm. For example, when practicing the method, iodinated casein can be added to the daily feed ration of the animal at about 100 ppm of the daily feed ration.

The animals, who are treated with thyroid-active substance, have above-normal blood levels of growth hormone or somatomedin. The above-normal or elevated blood levels of growth hormone or somatomedin are caused by artificial or exogenous administration of a growth hormone related substance. The administration of a growth hormone related substance can include the administration of growth hormone, (somatotropin), growth hormone releasing factor, somatomedin, or any substance that stimulates the production of endogenous growth hormone and subsequently the production of somatomedin. Substances that stimulate endogenous growth hormone include enkephalins or enkephalin-like compounds, prostaglandins, alpha-adrenergics, benzodiazapines, barbiturates, opiate antagonists, gamma-aminobutyric acid (GABA), GABAnergic compounds, and the like. Other substances that can be administered include any analogues of growth hormone or growth hormone releasing factor, such as methionyl bovine growth hormone, 29 amino acid growth hormone releasing factor, and the like.

The type of growth hormone related substance to be administered can be naturally or recombinantly derived or can be prepared by solid-phase synthetic procedures. In addition, the growth hormone or related substance does not have to be species specific. For example, porcine, bovine, or human growth hormone can be used in the administration of growth hormone to pigs.

The amount of growth hormone related substance needed to maintain an above-normal blood level of growth hormone in the animal is from about 5 mcg/kg/day (micrograms per kilogram per day) to about 300 mcg/kg/day. In pigs, the administration of from about 10 to about 300 mcg/kg of growth hormone will achieve an above-normal blood level. The preferred administration to pigs is from about 20 to about 100 mcg/kg/day.

Due to the protein nature of the growth hormone related substance, it is not desirable to administer it in an oral form. Intramuscular, intravenous, or subcutaneous injections can be used. In addition, the growth hormone related substance may be administered by implant. Typically, the animal can receive growth hormone related substance by parenteral route and can receive the thyroid-active substance by either an oral or parenteral route. However, the growth hormone related substance and thyroid-active substance can be administered parenterally in single drug delivery devices to achieve the desired effect. These devices include implants, microcapsules, pumps, and the like.

The effects of the administration of thyroid-active substances on the feed intake of pigs are shown in the following experiments.

TRIAL 1

Seventy-two crossbred (Yorkshire X Hampshire) barrows and gilts, weighing approximately 130 pounds, were placed in pens with 4 pigs to a pen. The animals were fed ad libitum with a swine corn/soy ration containing approximately 16% crude protein. Fresh water was also made available at all times.

The feed ration was comprised of the following ingredients:

| Ingredient | Percent by weight | Pounds/ Ton |
|---|---|---|
| Corn, yellow, ground | 76.70 | 1534 |
| Soybean Oil Meal, solvent extracted, dehulled, 50% | 19.35 | 387 |
| Calcium Carbonate | 1.20 | 24 |
| Dicalcium Phosphate, feed grade | 1.20 | 24 |
| Salt (sodium chloride) | 0.50 | 10 |
| Trace mineral premix, AN-03[1] | 0.10 | 2 |
| Swine Vitamin Premix, SW-03[2] | 0.65 | 13 |
| Vitamin A Premix, 3M USP units/pound[3] | 0.05 | 1 |
| Methionine Hydroxy Analogue, 93% | 0.20 | 4 |
| Selenium Premix[4] | 0.05 | 1 |
| | 100.00 | 2000 |

[1]Each kg (kilogram) of premix contains: 50 g (grams) manganese as manganese sulfate; 100 g zinc as zinc carbonate; 50 g iron as ferrous sulfate; 5 g copper as copper oxide; 1.5 g iodine as potassium iodide and 150 g maximum and 130 g minimum calcium as calcium carbonate.
[2]Each kg of premix contains: 77,161 IU Vitamin $D_2$; 2,205 IU Vitamin E; 411 mg riboflavin; 1,620 mg pantothenic acid; 2,205 mg niacin; 4.4 mg Vitamin $B_{12}$; 441 mg Vitamin K; 19,180 mg choline; 110 mg folic acid; 165 mg pyridoxine; 110 mg thiamine; and 22 mg biotin.
[3]Each kg of premix contains 6,613,800 IU Vitamin A.
[4]Each kg of premix contains 200 mg of selenium as sodium selenite.

The pigs were divided into three groups for treatment, with each group having 3 pens of barrows and 3 pens of gilts. The first group was used as the control and the other two groups were treated with 1.5 or 3.0 mg/day of pGH (porcine growth hormone) for the first 28 days of the trial. The dose was increased to 2.0 or 4.0 mg/day from day 29 to the end of the trial.

The hormone was put in solution using sterilized 0.2M (molar) potassium phosphate buffer (pH 7.8). (The buffer was prepared with pyrogen-free water.) The final concentration of pGH in the buffer was 1.0 mg/ml (milligrams per milliliter).

The treated pigs received a daily subcutaneous injection of the pGH solution in their flank areas. The injection volume for each group was as follows:

| | FORMULATION AND EXPERIMENTAL DESIGN | | | |
|---|---|---|---|---|
| | 0–28 days | | Day 29 to end | |
| Treatment Group | Carrier ml/day | pGH mg/day | Carrier ml/day | pGH mg/day |
| 1 | 3.0 | 0 | 4.0 | 0 |
| 2 | 1.5 | 1.5[a] | 2.0 | 2.0[a] |
| 3 | 3.0 | 3.0[a] | 4.0 | 4.0[a] |

[a]The concentration of the pGH solution was 1.0 mg/ml of carrier. [The solution concentration and injection volumes were chosen to deliver approximately 25 to 50 mcg/kg/day.]

The pigs were individually weighed at the beginning of the trial, every 14th day thereafter, and at the end of the trial. Pigs were removed from the trial when they reached approximately 230 pounds of body weight (in approximately 55 days).

The feed consumption for each pig was also recorded. The average daily feed intake and the average daily gain in pounds were calculated and recorded.

Table 1 shows the dosage-related reduction in feed intake.

TABLE 1

EFFECT OF PORCINE GROWTH HORMONE ON THE PERFORMANCE OF FINISHING SWINE

| TREATMENT | LEVEL MG/DAY | AVERAGE DAILY FEED | | AVERAGE DAILY GAIN | |
|---|---|---|---|---|---|
| | | POUNDS | PERCENT OF CONTROL | POUNDS | PERCENT OF CONTROL |
| CONTROL | 0 | 6.68 | | 1.78 | |

TABLE 1-continued

EFFECT OF PORCINE GROWTH HORMONE ON THE
PERFORMANCE OF FINISHING SWINE

| TREATMENT | LEVEL MG/DAY | AVERAGE DAILY FEED | | AVERAGE DAILY GAIN | |
|---|---|---|---|---|---|
| | | POUNDS | PERCENT OF CONTROL | POUNDS | PERCENT OF CONTROL |
| pGH | 1.5–2.0 | 6.43 | −3.7 | 1.86 | +4.5 |
| pGH | 3.0–4.0 | 6.05 | −9.4 | 1.85 | +3.9 |

TRIAL 2

TABLE 2

EFFECT OF pGH AND VARIOUS LEVELS OF IODINATED CASEIN
ON THE FEED INTAKE OF FINISHING SWINE

| TREAT | LEVEL MG/DAY | NO. OF PIGS | DAILY FEED INTAKE IN GRAMS DURING A 12-DAY TREATMENT PERIOD | | | | | | | | | | | |
|---|---|---|---|---|---|---|---|---|---|---|---|---|---|---|
| | | | DAY 1 | 2 | 3 | 4 | 5 | 6 | 7 | 8 | 9 | 10 | 11 | 12 |
| Control | | 3 | 2000 | 2000 | 2000 | 2000 | 2000 | 2000 | 2000 | 2000 | 2000 | 2000 | 2000 | 2000 |
| | | | 2000 | 2000 | 2000 | 2000 | 2000 | 2000 | 2000 | 2000 | 2000 | 2000 | 2000 | 2000 |
| | | | 2000 | 2000 | 2000 | 2000 | 2000 | 2000 | 2000 | 2000 | 2000 | 2000 | 2000 | 2000 |
| pGH | 9 | 3 | 2000 | 2000 | 2000 | 2000 | 2000 | 1520 | 1274 | 2000 | 2000 | 2000 | 2000 | 1261 |
| | | | 2000 | 2000 | 2000 | 1829 | 1447 | 1542 | 1738 | 1336 | 1155 | 1460 | 1417 | 1097 |
| | | | 2000 | 2000 | 2000 | 2000 | 1875 | 1730 | 2000 | 2000 | 2000 | 1798 | 1479 | 1763 |
| pGH + IC | 9 250 | 3 | 2000 | 2000 | 2000 | 2000 | 2000 | 2000 | 2000 | 2000 | 2000 | 2000 | 2000 | 2000 |
| | | | 2000 | 2000 | 2000 | 2000 | 2000 | 2000 | 2000 | 2000 | 2000 | 2000 | 2000 | 2000 |
| | | | 2000 | 2000 | 2000 | 2000 | 2000 | 2000 | 2000 | 2000 | 2000 | 2000 | 2000 | 2000 |
| pGH + IC | 9 500 | 3 | 2000 | 2000 | 2000 | 2000 | 2000 | 2000 | 2000 | 2000 | 2000 | 2000 | 2000 | 2000 |
| | | | 2000 | 2000 | 2000 | 2000 | 2000 | 2000 | 2000 | 2000 | 2000 | 2000 | 2000 | 2000 |
| | | | 2000 | 2000 | 2000 | 2000 | 2000 | 1798 | 2000 | 2000 | 2000 | 2000 | 1797 | 1817 |
| pGH + IC | 9 1000 | 2(a) | 2000 | 2000 | 2000 | 2000 | 2000 | 2000 | 2000 | 2000 | 2000 | 2000 | 2000 | 2000 |
| | | | 2000 | 2000 | 2000 | 2000 | 2000 | 2000 | 2000 | 2000 | 2000 | 2000 | 2000 | 1621 |

The pigs were limit-fed 1000 grams twice a day.
(a) One pig's temperature increased to 106 and 108° F. in the afternoon of days 6 and 7 and died on day 7. Its data is not included.

Fifteen crossbred barrows, each weighing approximately 90 kg, were maintained in individual stainless steel crates and fed swine corn/soy ration. All pigs were given a constant amount of feed, approximately 2000 g/day (grams per day), which was divided into two feedings of 1000 g/feeding (grams per feeding). Water was also mixed with the feed at the time of feeding.

The barrows were divided into 5 groups with each group consisting of 3 barrows. The groups were as follows:

1. Control (4.5 ml of carrier/day)
2. pGH (9 mg/day)
3. pGH (9 mg/day)+IC (250 mg/day)
4. pGH (9 mg/day)+IC (500 mg/day)
5. pGH (9 mg/day)+IC (1000 mg/day)

IC (iodinated casein) was used in Groups 3–5. One half of the daily dosage for each pig was mixed into the feed at each of the two-daily feedings.

The pGH solution was prepared as described in Trial 1, except that the concentration of pGH in the buffer was 2.0 mg/ml. The pGH was administered daily by subcutaneous injection in the flank area. The daily injections of solution were as follows:

| pGH REQUIREMENTS AND FORMULATIONS | | | | | |
|---|---|---|---|---|---|
| | Conc. (mg/ml) | ml/ inj. | mg pGH/ Pig | No. of Pigs | Daily Total (ml) | Daily Total (mg pGH) |
| Control | 0 | 4.5 | 0 | 3 | 13.5 | 0 |
| Treated | 2 | 4.5 | 9.0 | 12 | 54.0 | 108 |

The feed intake of each pig was recorded daily for a period of 12 days. The feed-intake results are shown in Table 2.

The animals were weighed at the beginning of the trial and at the end of 12 days. The 12-day weight gain for each group was calculated and recorded in pounds. The weight gain results are found in Table 3.

TABLE 3

EFFECT OF PORCINE GROWTH HORMONE AND
IODINATED CASEIN ON BODY WEIGHT GAIN OF
FINISHING SWINE

| TREATMENT | NO. OF PIGS | 12-DAY GAIN IN POUNDS |
|---|---|---|
| CONTROL | 3 | 22.3 |
| pGH (9 MG/DAY) | 3 | 22.7 |
| pGH (9 MG/DAY) + IC (250 MG/DAY) | 3 | 31.3 |
| pGH (9 MG/DAY) + IC (500 MG/DAY) | 3 | 29.3 |
| pGH (9 MG/DAY) + IC (1000 MG/DAY) | 2 | 28.0 |

We claim:

1. A method of offsetting feed intake depression in pigs attributable to exogenous administration of a growth hormone related substance, which comprises administering an effective amount of a thyroid-active substance to the pigs.

2. The method of claim 1 wherein the thyroid-active substance is iodinated casein.

3. The method of claim 2 wherein the iodinated casein is administered orally on a daily basis.

4. The method of claim 3 wherein the iodinated casein is administered through feedstuff at a rate of from 1 to 1000 ppm.

5. The method of claim 4 wherein the iodinated casein is administered at a rate of from 5 to 250 ppm.

6. The method of claim 5 wherein the iodinated casein is administered for 1 to 5 months.

7. The method of claim 1 wherein the thyroid-active substance is administered by implant.

8. The method of claim 2 wherein the growth hormone related substance is growth hormone.

9. The method of claim 8 wherein the growth hormone is recombinant growth hormone.

10. The method of claim 9 wherein the growth hormone is porcine growth hormone.

11. The method of claim 10 wherein the amount of growth hormone is from 10 to 300 mcg/kg/day.

* * * * *